(12) United States Patent
Farkas et al.

(10) Patent No.: US 6,795,554 B2
(45) Date of Patent: Sep. 21, 2004

(54) METHOD OF TRANSMITTING MEDICAL INFORMATION OVER A NETWORK

(75) Inventors: Richard A. Farkas, Bloomfield Hills, MI (US); Christopher J. Cooper, Vancouver (CA)

(73) Assignee: Inner Vision Imaging, LLC, Farmington Hills, MI (US)

( * ) Notice: Subject to any disclaimer, the term of this patent is extended or adjusted under 35 U.S.C. 154(b) by 664 days.

(21) Appl. No.: 09/827,003

(22) Filed: Apr. 5, 2001

(65) Prior Publication Data

US 2002/0146124 A1 Oct. 10, 2002

(51) Int. Cl.[7] .................... H04K 1/10; G06F 17/60
(52) U.S. Cl. .................. 380/33; 380/279; 713/21; 705/3
(58) Field of Search ............... 380/33, 34, 211, 380/279; 713/160, 179, 200, 201; 705/2, 3

(56) References Cited

U.S. PATENT DOCUMENTS

| | | | |
|---|---|---|---|
| 5,995,939 A | * | 11/1999 | Berman et al. ............... 705/3 |
| 6,032,119 A | | 2/2000 | Brown et al. ................. 705/2 |
| 2001/0031997 A1 | | 10/2001 | Lee .............................. 607/59 |

FOREIGN PATENT DOCUMENTS

EP            0 884 670 A1    12/1998    ............. G06F/1/00

OTHER PUBLICATIONS

"Biodata ensures compliance with HIPAA Regulations; Advanced Acoustical Concepts Uses BabylonMETA To Deliver Encryption To Its Telemedicine Customers" Business Wire, Nov. 30, 2000.

* cited by examiner

*Primary Examiner*—Justin T. Darrow
(74) *Attorney, Agent, or Firm*—Gifford, Krass, Groh, Sprinkle, Anderson & Citkowski, P.C.

(57) ABSTRACT

A method for transmitting medical information relating to a patient over a network, such as a telecommunication network. The medical information includes both patient identifiable data as well as patient medical condition/treatment data. The method includes the first step of encrypting the patient identifiable data and then transmitting both the encrypted patient identifiable data and the unencrypted patient medical condition/treatment data over the network. The network preferably includes two channels, and the encrypted patient identifiable data is transmitted over one channel while the unencrypted patient medical condition/treatment data is transmitted over the other channel.

4 Claims, 1 Drawing Sheet

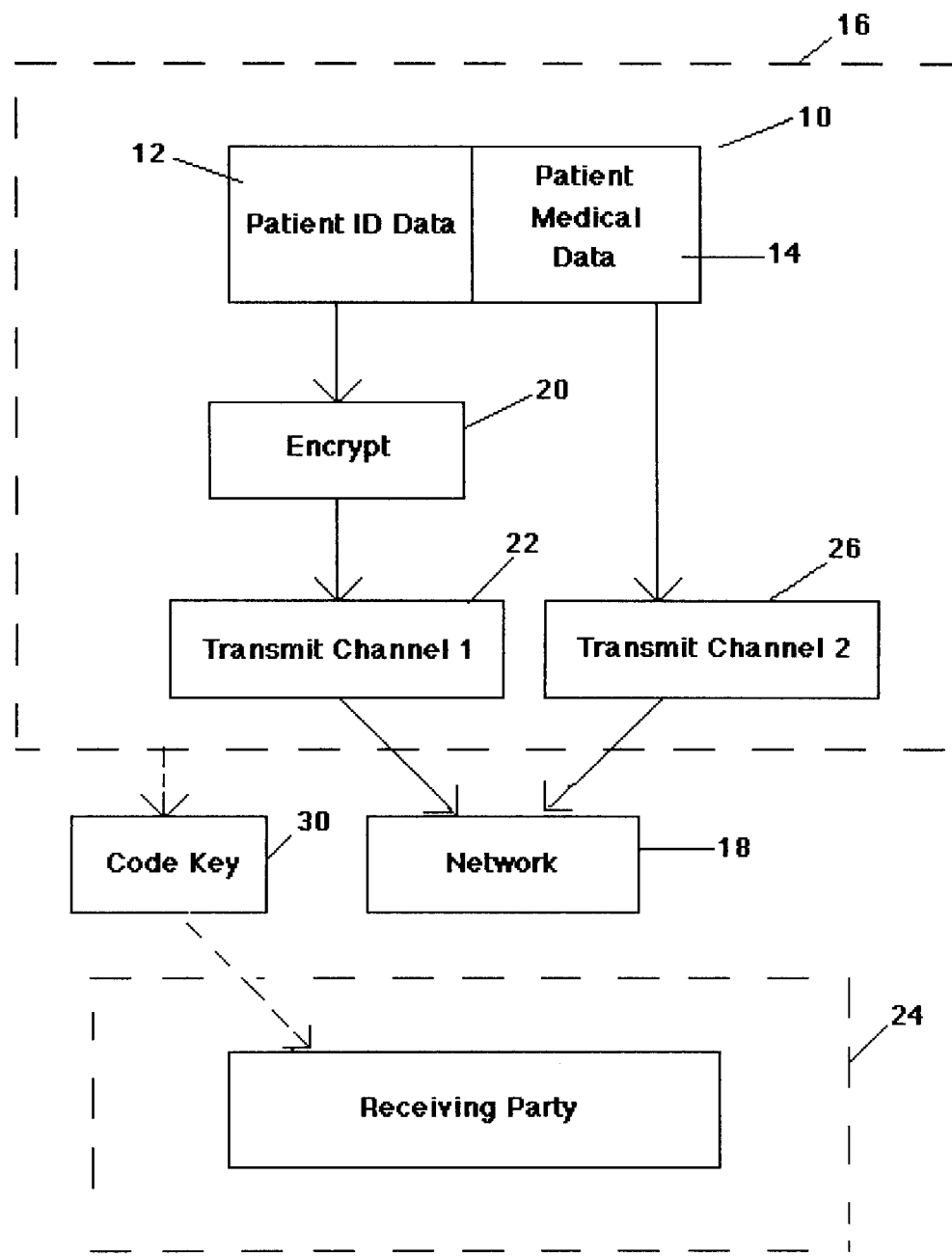

METHOD OF TRANSMITTING MEDICAL INFORMATION OVER A NETWORK

BACKGROUND OF THE INVENTION

I. Field of the Invention

The present invention relates to a method for transmitting medical information over a network.

II. Description of Related Art

Medical information relating to a patient is commonly transmitted over networks, such as a telecommunication network. The medical information includes both patient identifiable data as well as patient medical condition/treatment data (hereinafter referred to as "patient medical condition data"). Such patient medical condition data may include not only textual data but also images and audio. Furthermore, such images and audio may be transmitted over the network on a real-time basis, e.g. at thirty frames/second.

In order to protect patient privacy with respect to their medical records, the United States federal government has recently enacted the Health Insurance Portability and Accountability Act (HIPAA). In essence, HIPAA protects the patient's right to privacy to their own medical records.

In order to comply with HIPAA, several attempts have been made to encrypt all the patient information, i.e. both the patient identifiable data as well as the patient medical condition data, and then transmit the encrypted data over the network. However, the encryption of the patient medical condition data requires extensive computing power both at the transmitting and receiving end since the medical condition data is typically extensive, particularly if it includes images. Furthermore, the encryption of medical condition data on a real-time basis, e.g. thirty frames per second, renders the encryption of such medical condition data impractical, even with extensive computing power. For that reason, such previously known methods have not proven wholly successful or acceptable in use.

SUMMARY OF THE PRESENT INVENTION

The present invention provides a method for encrypting medical information which overcomes all of the above-mentioned disadvantages of the previously known attempts.

In brief, the method of the present invention includes the step of encrypting only the patient identifiable data and then transmitting the encrypted patient identifiable data over the network. Such patient identifiable data would include, for example, the patient's name, Social Security number, address, fingerprint information, as well as other information from which the patient could be readily identified. The method of the present invention then transmits the encrypted patient identifiable data as well as the unencrypted patient medical condition data over the network. Since the patient medical condition data cannot be correlated with a particular patient, the privacy of the medical records of that patient is preserved.

In practice, the method of the present invention operates most efficiently over a telecommunications network having two channels. The first channel comprises a text channel while, conversely, the second channel comprises a video/audio channel. The encrypted patient identifiable data is then transmitted over the text channel while the unencrypted patient medical condition data is transmitted over the audio/video channel.

In order to enable both the transmitting and receiving ends of the network to identify the patient and correlate that patient's medical condition data to the patient, a code key is optionally assigned to the individual patient. That code key can then be transmitted either over the network at a time temporally spaced from the transmission of the encrypted patient identifiable data and unencrypted patient medical condition data, or may be transmitted by completely separate means. For example, assuming that both the transmitting and receiving ends include software to decode the encrypted patient identifiable data, a code key is assigned at the transmitting end of the network. This code key is then transmitted to the receiving end of the network in a fashion so that the code key cannot be correlated with the transmission of the transmitted medical information.

BRIEF DESCRIPTION OF THE DRAWING

A better understanding of the present invention will be had upon reference to the drawing which is a diagrammatic chart illustrating a preferred embodiment of the method of the present invention.

DETAILED DESCRIPTION OF A PREFERRED EMBODIMENT OF THE PRESENT INVENTION

With reference to the drawing, patient medical information 10 is there shown diagrammatically. This patient information 10 includes both patient identifiable data 12 and patient medical data 14.

The patient identifiable data includes all data from which the patient may be identified. Such data includes, for example, the patient's name, Social Security number, address, fingerprint information and the like. Conversely, the patient medical data includes data relating to the patient's medical condition or treatment. Such patient medical data 14 can include, for example, images and audio which may be in real time. The patient's medical information 10, furthermore, is contained at a transmitting party 16 to a network 18.

The patient's identifiable data 12 is first encrypted at 20 using any conventional encryption method. The encryption data is then transmitted at 22 over the network 18 to a receiving party 24. Conversely, the unencrypted patient medical data 14 is transmitted in unencrypted format at 26 over the network 18 to the receiving party 24.

Preferably, the network 18 comprises a telecommunication network having at least two channels. A first channel comprises a text channel while a second channel comprises an audio/video channel. Consequently, the encrypted patient identifiable data 12 is transmitted over the text channel of the network 18 while, conversely, the patient medical data is transmitted over the audio/video channel of the network 18.

The transmission of the patient medical data, furthermore, may be in real time. Typically, over a conventional telecommunication network, the real-time transmission of audio/video data occurs at thirty frames per second for the video transmission.

The receiving party 24 receives both the encrypted patient identifiable data as well as the unencrypted patient medical data from the network 18. Since only encrypted patient identifiable data is transmitted by the transmitting party 24, patient privacy is maintained even if an unauthorized party intercepted transmissions over the network 18. Furthermore, since the patient identifiable data is encrypted prior to transmission over the network 18, an unauthorized party intercepting such transmission would be unable to correlate that medical condition data with a particular patient thus preserving the privacy of the patient.

In some cases, however, it may be desirable for the receiving party 24 to identify the particular patient, perhaps for correlating that particular patient with medical records previously received by the receiving party 24 for that particular patient. In that event, a code key 30 may be generated by the transmitting party 16 and forwarded to the receiving party 24 in any conventional fashion. For example, the code key 30 could be transmitted over the network 18 at a time temporally spaced from the transmission of the patient medical condition data 14. Other simpler means, such as transmitting the code key 30 to the receiving party 24 by facsimile, can also be utilized.

From the foregoing, it can be seen that the present invention provides a simple and yet effective method for transmitting medical data and patient information over a network while still preserving the privacy of the patient from unwanted interception of data over the network. Having described our invention, however, many modifications thereto will become apparent to those skilled in the art to which it pertains without deviation from the spirit of the invention as defined by the scope of the appended claims.

We claim:

1. A method for transmitting medical information relating to a patient over a network, said medical information including patient identifiable data and patient medical condition/treatment data, said method comprising the steps of:

encrypting the patient identifiable data, and transmitting the encrypted patient identifiable data and the unencrypted patient medical condition/treatment data over the network, wherein the network comprises a teleconferencing network having at least two separate channels, wherein said transmitting step further comprises the steps of transmitting the encrypted patient identifiable data over one channel and retransmitting the unencrypted patient medical condition/treatment data over the other channel.

2. The method as defined in claim 1 wherein said encrypting step further comprises the steps of creating a code key necessary to decode the encrypted patient identifiable data, and transmitting said key over the network.

3. The method as defined in claim 1 wherein said one channel comprises a text channel and wherein said other channel comprises a video channel.

4. The method as defined in claim 1 wherein said transmitting step further comprises the step of assigning an arbitrary indicia to the patient, and transmitting said arbitrary indicia over the network.

* * * * *